US009656024B2

(12) United States Patent
Eggert et al.

(10) Patent No.: US 9,656,024 B2
(45) Date of Patent: *May 23, 2017

(54) MEDICAMENT DELIVERY DEVICE WITH CAP

(71) Applicant: Sanofi-Aventis Deutschland GmbH, Frankfurt am Main (DE)

(72) Inventors: Ilona Eggert, Frankfurt am Main (DE); Aidan Michael O'Hare, West Midlands (GB); Barry Yates, Warwickshire (GB); Aled Meredydd James, West Midlands (GB); John E. Hayes David Cross, Northhamptonshire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/080,941

(22) Filed: Mar. 25, 2016

(65) Prior Publication Data

US 2016/0346482 A1  Dec. 1, 2016

Related U.S. Application Data

(63) Continuation of application No. 14/119,722, filed as application No. PCT/EP2012/059756 on May 24, 2012, now Pat. No. 9,295,784.

(30) Foreign Application Priority Data

May 25, 2011 (GB) .................. 11167537.7

(51) Int. Cl.
*A61M 5/32* (2006.01)
*G06F 1/32* (2006.01)
(Continued)

(52) U.S. Cl.
CPC ........ *A61M 5/3202* (2013.01); *A61M 5/2053* (2013.01); *A61M 5/24* (2013.01);
(Continued)

(58) Field of Classification Search
CPC ................ A61M 5/3202; A61M 5/172; A61M 5/16827; A61M 5/1689;
(Continued)

(56) References Cited

U.S. PATENT DOCUMENTS

| 6,514,230 B1 | 2/2003 | Munk et al. |
| 9,295,784 B2* | 3/2016 | Eggert .................. G06F 1/3234 |
| 2006/0175427 A1 | 8/2006 | Jonientz et al. |

FOREIGN PATENT DOCUMENTS

| EP | 1640029 A1 | 3/2006 |
| JP | 2003511157 A | 3/2003 |

(Continued)

*Primary Examiner* — Manuel Mendez
(74) *Attorney, Agent, or Firm* — McDonnell Boehnen Hulbert & Berghoff LLP

(57) ABSTRACT

The invention resides in a hand-held medicament delivery device which comprises a housing containing a first electrical circuit and a battery, a medicament delivery mechanism, and a protective cap releasably securable to the housing. The housing also includes a contactless switch and the cap a switch actuator. The switch is operable between an on state in which the first electrical circuit is connected to the battery and an off state in which the first electrical circuit is disconnected from the battery. The invention also resides in a method of controlling power in a hand held medicament delivery device comprising the steps of actuating a contactless switch in the housing by an actuator in a housing cap when the switch and actuator are in proximity, the actuation of the switch signalling to a microprocessor that the cap is on the housing, detecting the status of the device by the (Continued)

microprocessor, and only if the microprocessor determines the device is inactive, powering down the device.

20 Claims, 5 Drawing Sheets

(51) Int. Cl.
*A61M 5/20* (2006.01)
*A61M 5/24* (2006.01)
*A61M 5/30* (2006.01)
*A61M 5/315* (2006.01)
*G06F 19/00* (2011.01)
*A61M 5/31* (2006.01)

(52) U.S. Cl.
CPC .......... *A61M 5/30* (2013.01); *A61M 5/3158* (2013.01); *A61M 5/31546* (2013.01); *G06F 1/3231* (2013.01); *G06F 1/3234* (2013.01); *G06F 1/3296* (2013.01); *G06F 19/3456* (2013.01); *A61M 2005/3126* (2013.01)

(58) Field of Classification Search
CPC ........... A61M 2205/6018; A61M 2005/14208; A61M 5/1723; A61M 5/14244; A61M 5/16854; A61M 5/14276; A61M 5/365; A61M 5/2053; A61M 5/24; A61M 5/30; A61M 5/31546; A61M 5/3158; A61M 2005/3126; G06F 1/3234; G06F 19/3456; G06F 1/3231; G06F 1/3296; A61B 5/14532
USPC .... 604/65–67, 131, 151; 128/DIG. 1, 12, 13
See application file for complete search history.

(56) References Cited

FOREIGN PATENT DOCUMENTS

| WO | 9733638 | A1 | 9/1997 |
|----|---------|----|--------|
| WO | 0126710 | A2 | 4/2001 |
| WO | 2004010231 | A2 | 1/2004 |
| WO | 2005004956 | A1 | 1/2005 |
| WO | 2006032614 | A1 | 3/2006 |
| WO | 2010037828 | A1 | 4/2010 |

* cited by examiner

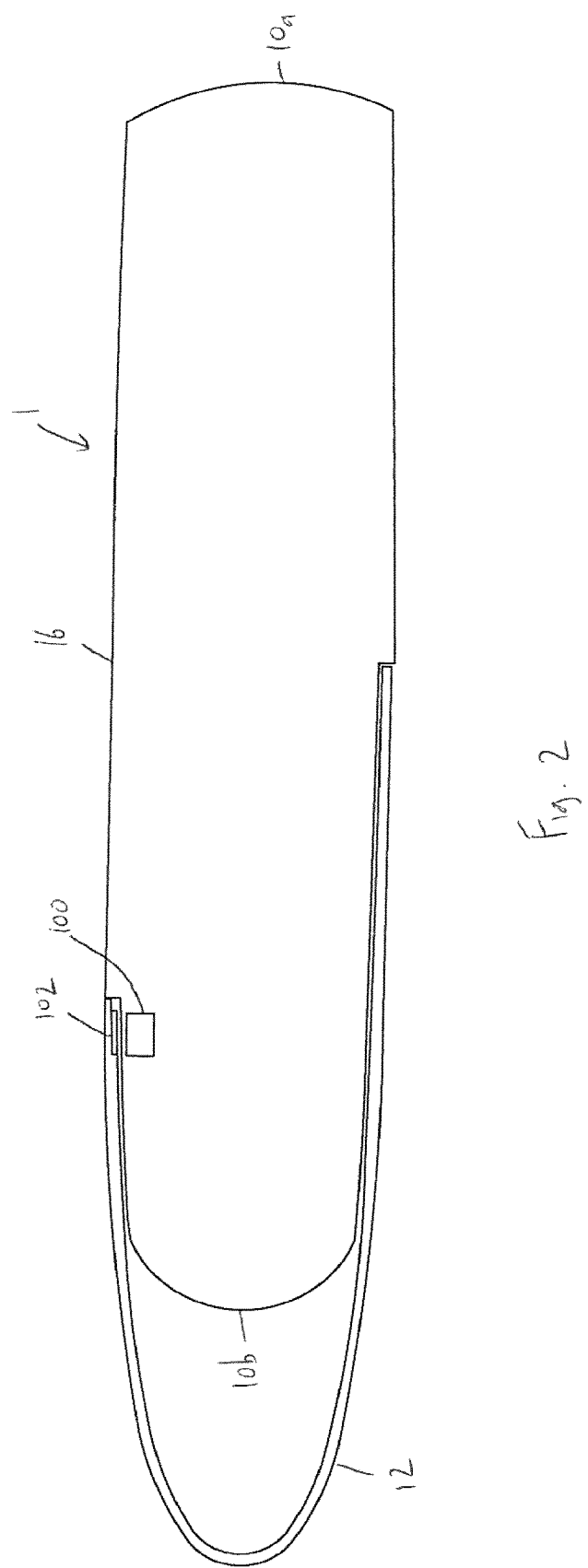

MEDICAMENT DELIVERY DEVICE WITH CAP

CROSS REFERENCE TO RELATED APPLICATIONS

The present application is a continuation of U.S. patent application Ser. No. 14/119,722 filed Nov. 22, 2013, now U.S. Pat. No. 9,295,784, which is a U.S. National Phase Application pursuant to 35 U.S.C. §371 of International Application No. PCT/EP2012/059756 filed May 24, 2012, which claims priority to European Patent Application No. 11167537.7 filed May 25, 2011. The entire disclosure contents of these applications are herewith incorporated by reference into the present application.

The present invention relates to an electro-mechanical handheld medicament delivery device having a cap.

Certain medical conditions require patients to self-administer medicament(s) over a long period of time, perhaps years. Where possible such medicaments will be formulated for oral delivery which helps with patient compliance. Due to the nature of the medicament (e.g. insulin) oral delivery is not always possible and other administration routes are necessary. Self administration by injection is not ideal, inter alia for reasons of accurate dosing and patient compliance (needle-phobia being relatively common), but oftentimes necessary.

Over recent years there has been significant development in the area of injectors. In particular electro-mechanical injectors are now available. Such devices are generally battery powered and designed for multiple uses. The devices generally comprise a housing having a motor-driven piston which acts on a cartridge containing the medicament to be delivered through a needle attached to the device (although it will be understood that "electro-mechanical device" includes any device that requires power for any reason, irrespective of whether medicament delivery is by electro-mechanical or purely mechanical means). The device may have a graphical display for displaying such information as device status (e.g. ready for injection, cartridge empty, error status, dosing history etc.) a user interface (usually one or more buttons) for entering a required dose, initiating dosing and/or priming and powering up/down the device and a microprocessor for controlling the motor(s) according to a user defined dose, monitoring error conditions, writing dose histories to memory etc.

Certain devices are available for delivering a combination of two medicaments from separate cartridges, each cartridge being driven by a separate motor. For ease of use the display and the user interface may be illuminated. It will therefore be appreciated that there can be a significant power demand from such devices. There is therefore a need to minimise the power drawn by such devices, particularly when not in use between injections, a state in which the device will spend most of its time, to extend the interval between battery charges or replacement. The present invention is conceived with this problem in mind.

The users of devices with which the present invention is concerned may have complicating medical conditions. Lack of manual dexterity, visual impairment and memory loss are not uncommon. Thus, any solution to powering down the device should ideally not require any additional specific tasks for the user.

Devices are known that simply use the presence of a cap to power down the device. For example the Innovo™ device previously sold and marketed by Novo Nordisk uses a tab in the cap to prise apart two contacts in the housing. The tab inserts into a slot in the surface of the housing. This has the disadvantage of potentially allowing the ingress of moisture or dust into the housing or requires a gasket or other means to seal the slot. A significant advantage of the present invention is that the contactless nature of the switch means that no additional openings for potential ingress of water or dust are created. Moreover, there is always the risk that a mechanical switch will fail through repeated use.

WO 2006/032614 describes an injection device with a cap, such that when the cap is placed onto the device, the device switches between an injection mode and a set-up mode. Both modes are controlled by a common electrical circuit. With the cap on the device, the device must either be manually turned off, or a time-out feature must be used to switch off the device. Both of these solutions lead to unnecessary on-time for the device.

Use of a mechanical switch can be avoided simply by providing the device with a time out mechanism. However, this will inevitably lead to periods before timing out when the device is fully powered when inactive, adversely affecting battery life.

According to a first aspect of the present invention there is provided a hand-held medicament delivery device comprising:
a housing containing a first electrical circuit and a battery
a medicament delivery mechanism, and
a protective cap releasably securable to the housing,
wherein the housing includes a contactless switch and the cap a switch actuator configured to activate the contactless switch, and wherein the switch is operable between an on state in which the first electrical circuit is connected to the battery and an off state in which at least part of the first electrical circuit is disconnected from the battery.

As used herein "contactless switch" means that there is no direct physical contact between the switch in the housing and the actuator in the cap.

The nature of the delivery mechanism is not particularly limited and may be purely mechanical, e.g. user operated plunger or electro-mechanical, e.g. a motor driven piston.

The device may be a jet injector in which case the drug delivery mechanism will include a nozzle or a needle injector in which case the drug delivery mechanism will include a needle. Conveniently, the housing is configured to receive the cap over the nozzle or needle.

In certain embodiments the cap and housing are asymmetric such that there is only a single configuration in which the cap is securable to the housing.

Any known mechanism may be used for releasably securing the cap to the housing including push/friction fit or snap fit components or a latching mechanism.

The device may optionally include a graphical display. The device may also include a user interface (e.g. one or more buttons) for programming the device.

In certain embodiments, the switch is arranged to disconnect the first electrical circuit from the battery when in proximity to the switch actuator (i.e. when the cap is in place on the housing).

In certain embodiments, the switch is arranged to connect the first electrical circuit to the battery when the switch actuator is not in proximity to the switch actuator (i.e. when the cap is off the housing).

The switch could be, for example an optical switch, a Hall sensor switch, a capacitive sensor switch an ultrasonic sensor switch, an induction switch or a reed switch. In certain embodiments the switch is a reed switch, the switch actuator being a magnet. The skilled person will appreciate that the contacts within a reed switch can be normally open or closed such that actuation causes them to close or open respectively. In certain embodiments, the reed switch contacts are normally closed such that they open on actuation. In such embodiments no current can flow through the first circuit when the switch is actuated.

In certain embodiments, the device will include a microprocessor (for example a programmable microprocessor having memory and input/output functionality) and/or a second electrical circuit. In such embodiments power is always maintained to the second electrical circuit (for example to power a real time clock). It will be understood that the first electrical circuit is the primary circuit which will ideally power, if present, the motor(s), display, any illumination and any other functionality not required when the device is not in use, whereas the second (auxiliary) circuit will power only those essential functions required when the device is not in use so as to minimise power consumption.

In a particular configuration, actuation of the switch is not used to directly power down the first electrical circuit, but signals its actuation (i.e. cap on) to the microprocessor. The microprocessor disconnects power to the first electrical circuit only with a variable delay after confirming it is safe to do so, e.g. any motors are not running, no injection is in progress and all tasks have been written to memory. Such an arrangement is particularly advantageous in that it prevents accidental actuation of the switch, for example by stray magnetic fields.

In a second aspect, the invention resides in a method of controlling power in a hand held medicament delivery device comprising
actuating a contactless switch in the housing by an actuator in a housing cap when the switch and actuator are in proximity, the actuation of the switch signalling to a microprocessor that the cap is on the housing,
detecting the status of the device by the microprocessor, and only if the microprocessor determines the device is inactive, powering down the device.

In a variation of the above method, the device may be configured such that the microprocessor powers down a primary electrical circuit whilst power is maintained to a second auxiliary circuit.

The method of the second aspect of the invention may utilise a device in accordance with the first aspect.

The term "medicament delivery device" as used herein, means a device capable of administering a dose of one or more medicaments to a patient. Such devices may administer fixed and/or variable doses of medicament to a patient. Handheld medicament delivery devices are sometimes called 'pen-type' devices. The medicament delivery mechanism employed by such devices is preferably electromechanical, utilising a motor and gearing to drive a piston rod, although manual delivery mechanisms incorporated into electrically controlled or configured devices may also be envisaged.

The term "drug" or "medicament", as used herein, means a pharmaceutical formulation containing at least one pharmaceutically active compound,
wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compounds,
wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis,
wherein in a further embodiment the pharmaceutically active compound comprises at least one peptide for the treatment and/or prophylaxis of diabetes mellitus or complications associated with diabetes mellitus such as diabetic retinopathy,
wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)des(B30) human insulin and B29-N-(ω-carboxyhepta-decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopaedia of Pharmaceutical Technology.

Pharmaceutically acceptable solvates are for example hydrates.

The invention will now be further described by way of example with reference to the accompanying drawings, in which:

FIG. 2 is a simplified cross-sectional view of the device of FIG. 1b, showing the cap, a contactless switch and a switch actuator;

References to the device in the following detailed description are intended to refer to the device as referenced in the appended figures and not to when the device is in a use state. Furthermore, the figures are intended to be schematic representations to highlight relevant functionality of the present invention and therefore unnecessary structures have been omitted from the device for clarity. The relative dimensions of the device are also illustratory only. Reference to 'distal' and 'proximal' are intended to refer to the end of the device where medicament delivery occurs and the opposite end pointing away from the delivery site respectfully.

Figure 1A:
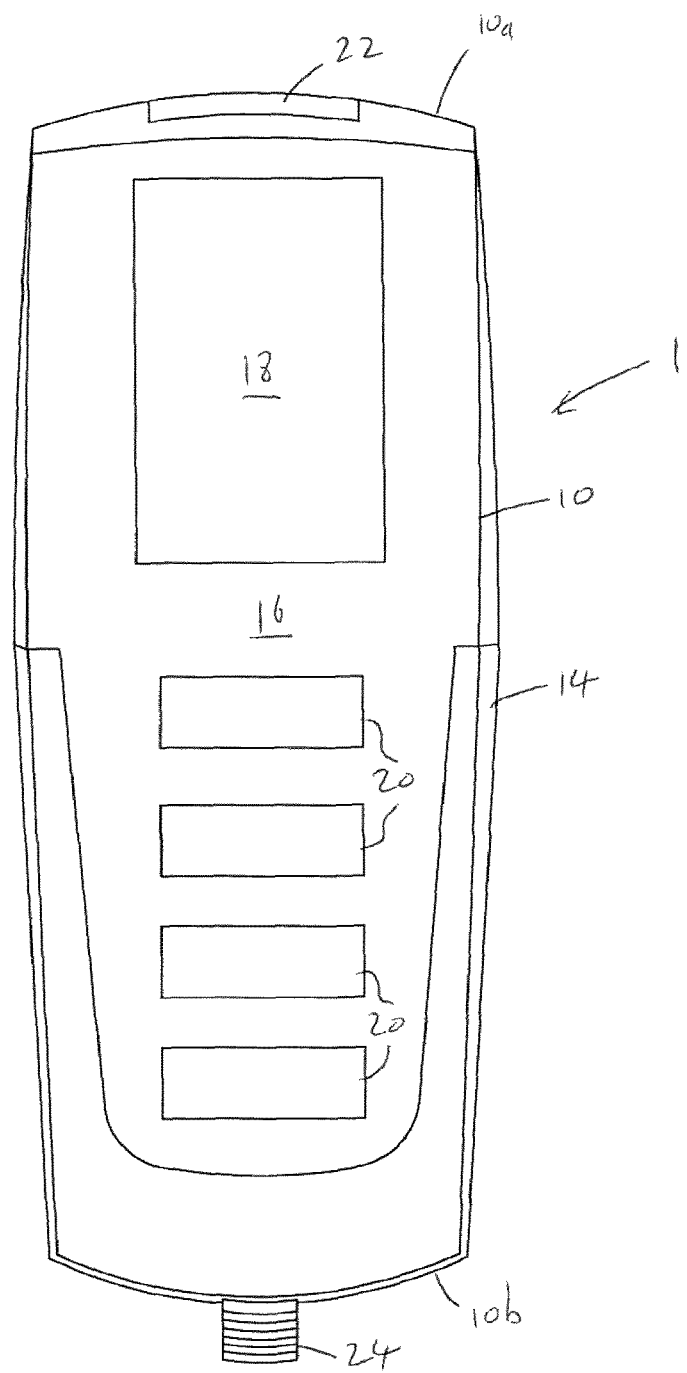
FIG. 1a is a plan view of a medicament delivery device according to the present invention with cap off.

The medicament delivery device 1 illustrated in FIG. 1 comprises a housing 10 having a proximal end 10a and a distal end 10b. At the distal end 10b, a removable end cap or cover 12 is provided. This end cap 12 and the housing 10 (at its proximal end) are shaped to provide a form fit connection so that once the cap 12 is slid onto the distal end 10b of the housing 10, the frictional fit between the cap 12 and the housing 10 prevents the cap from inadvertently falling off the housing 10. It will be understood that in other embodiments (not shown) other means of releasably securing the cap to the housing such as snap-fit may be employed.

The interior surface of the cap 12 and the outer surface of the housing 10 at its proximal end 10b are shaped such that there is only one possible configuration in which the cap 12 properly fits onto the distal end 10b of the housing 10. Such an arrangement is preferable because it provides certainty in the alignment of components of the cap 12 with components of the housing 10, as will be explained below.

The housing 10 contains a microprocessor control unit upon a PCB, an electro-mechanical drive train, a battery, and at least one medicament reservoir (described with reference to FIG. 3). A cartridge holder 14 can be removably attached to the housing 10 and may contain one or more cartridges of medicament. The cartridge holder 14 is configured so as allow the replacement of the medicament cartridges as necessary. The medicament delivery device 1 can be used to administer a computed dose of a medicament (or medicaments) through a needle assembly, such as a double ended needle assembly. It will be understood that the cap and housing arrangement described is equally applicable to needleless jet injectors.

A control panel region is provided on one major face 16 of the housing 10 and comprises a digital OLED display 18 towards the distal end 10a of the housing 10 along with a plurality of human interface elements (buttons 20 in the embodiment shown) that can be manipulated by a user to set and inject a medicament dose. It will be understood that in other embodiments (not shown) different display technology such as LC displays can be used. The buttons 20 also allow navigation through menu structures displayed on the OLED display 18. A dose button 22 is provided in a minor face of the housing 10 at its proximal end 10a. At the distal end of the housing is provided a screw-threaded needle mount 24. The needle mount 24 is configured to receive a needle hub (not shown). This needle hub can be configured to allow a dose dispenser, such as a conventional pen type injection needle assembly, to be removably mounted to the housing 10. It will be understood that the attachment between the needle mount 24 and a needle hub is preferably a screw fit to allow standard 'type A' needles to be fitted to the needle mount 24, although other attachment mechanisms as known in the art, such as Luer lock attachments may be used in other embodiments (not shown).

In use, when the device is turned on, the digital display 18 shown in FIG. 1 illuminates and provides the user certain device information, preferably information relating to the medicaments contained within the cartridge holder 14. For example, the user is provided with certain information relating to both the contents of the cartridge and previous dose history.

Figure 1B:
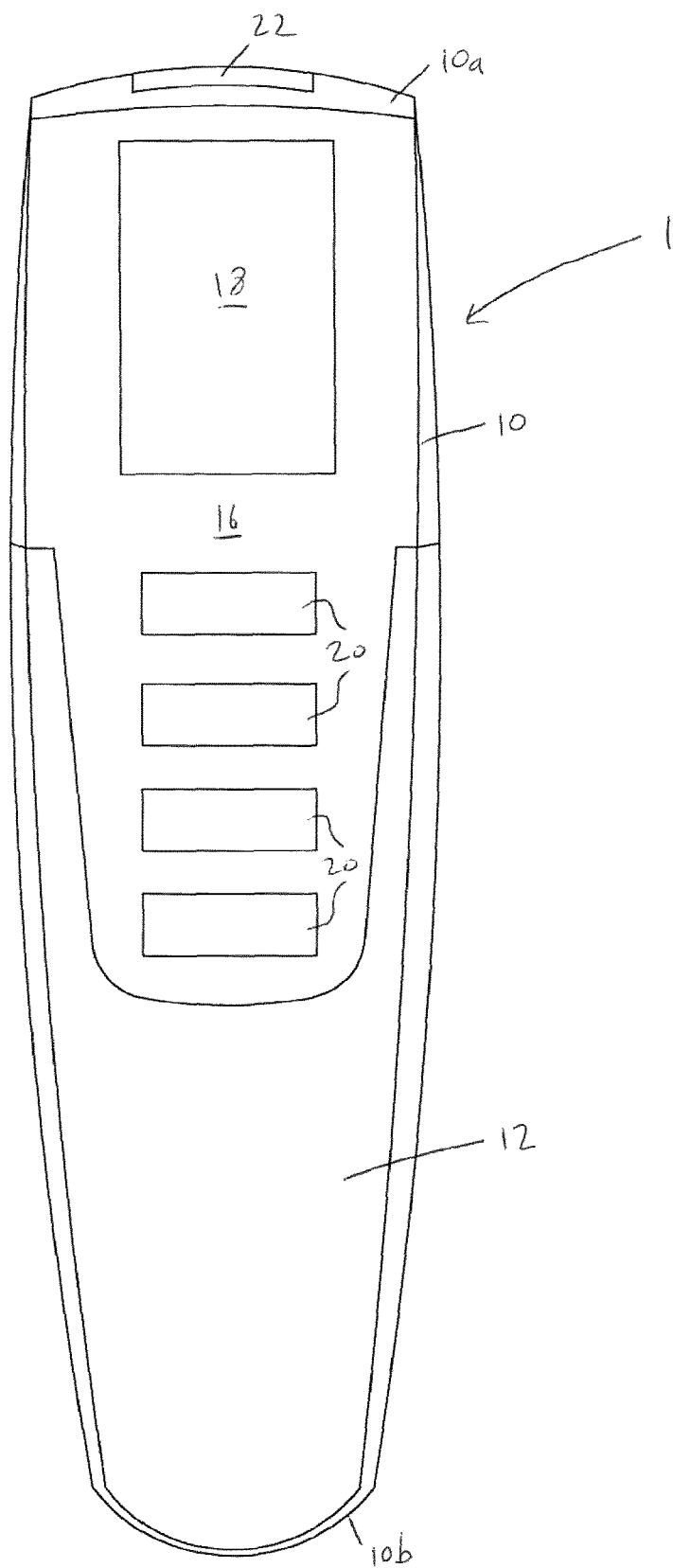
FIG. 1b is a plan view of the device illustrated in FIG. 1a with the cap in place.

FIG. 2 is a cross-sectional view through the medicament delivery device 1 shown in FIG. 1b showing the location of a contactless switch in the form of a reed switch 100 below the surface of the major face 16 of the housing 10 and a corresponding contactless switch actuator in the form of a magnet 102 mounted to an interior surface of the cap. Alternative arrangements for the contactless switch (not shown) include a Hall switch, inductive switch or the like. As noted above, the cap 12 of the device 1 is configured to fit onto the housing 10 in one predetermined orientation. As may be seen in FIG. 2, when the cap 12 and the housing 10 are correctly aligned, the reed switch 100 and the magnet 102 are closely spaced such that the magnet activates the reed switch 100 to indicate to the device 1 that the cap 12 has been placed (correctly) onto the housing 10.

Figure 3:
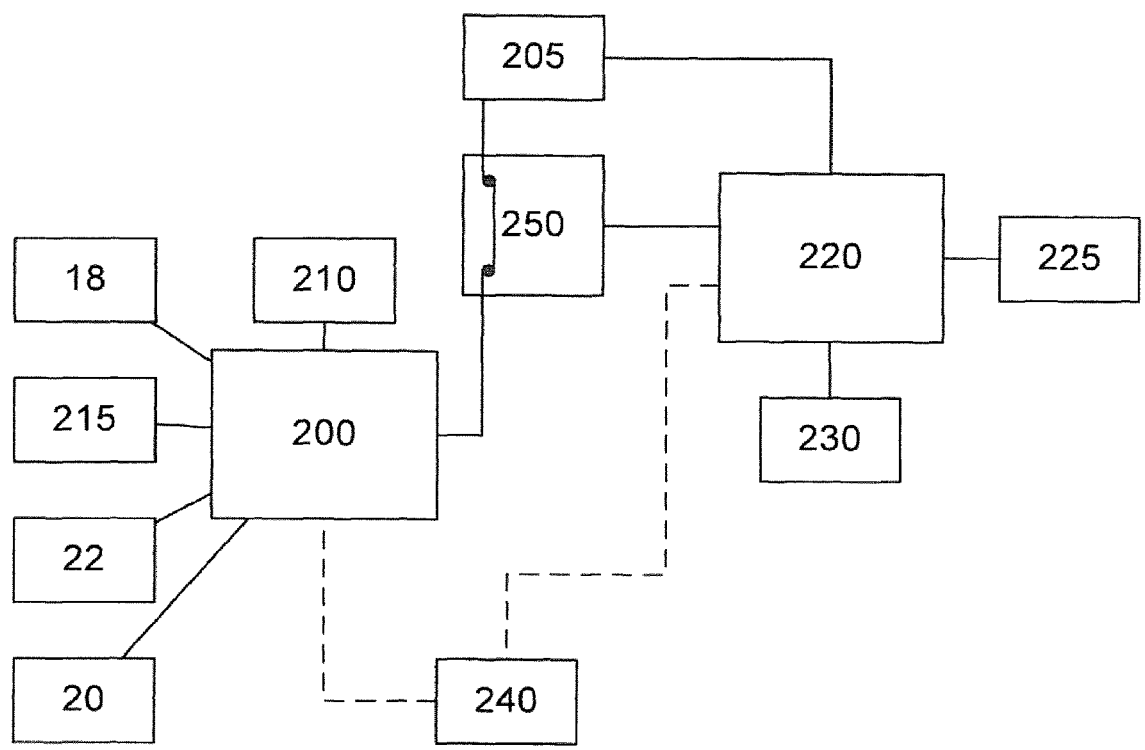
FIG. 3 is a block diagram illustrating schematically the functionality of the device illustrated in FIG. 1.

FIG. 3 is a block diagram outlining the key electrical circuitry for the embodiment of FIGS. 1 and 2. The housing 10 contains a first electrical circuit 200 which is connected to a battery 205 that powers a stepper motor 210 which can inject the dose to be delivered. In other embodiments it will be understood that BLDC or induction motors may be employed, or the motor may be replaced by an equivalent mechanical actuation means. Also connected to the first electrical circuit 200 is the OLED display 18, the user buttons 20 and dose button 22. All of the user buttons 20 and dose button 22 are illuminated with LEDs 215 although it should be noted that other forms of illumination, illumination of only a subset of the buttons or no illumination at all are all possibilities. It will be appreciated that certain features, such as the motor 210, may be replaced by an equivalent manual mechanism. In such case, sensors may be employed on the mechanical components to identify the state of such components and to relay the state of the components to the first electrical circuit 200. It may also be appreciated that other components may be present on the electrical circuits 200, 220, including for example but not limited to memory and sensors.

The housing 10 also contains a secondary electrical circuit 220. The role of the secondary electrical circuit 220 is to act as a monitoring circuit. Connected to the secondary electrical circuit 220 is a clock 225 that maintains the device system time and a cap switch 230 comprising the reed switch 100 and magnet 102 (FIG. 2). Also contained within the housing are a MPU (microprocessor) 240 and an electrical switching circuit 250. The electrical switching circuit 250 controls the electrical connection between the first electrical circuit 200 and the battery 205. Operation of the electrical switching circuit 250 is controlled by the second electrical circuit 220. In the present invention the electrical switching circuit 250 is a power supply circuit, although embodiments of the invention may utilise a switch relay. Furthermore, it will be appreciated that the electrical switching circuit 250 and/or the microprocessor 240 can be incorporated into the first or second electrical circuits 200, 220.

It may be seen from FIG. 3 that the substantial work of the device is carried out by the first electrical circuit 200. As such, isolating the first electrical circuit 200 from the battery 205 when the first electrical circuit 200 is not in use greatly reduces the power consumption of the device, increasing the battery life. The second electrical circuit 220, whilst still connected to the battery, is able to operate with a much lower power signature than the first electrical circuit 200, due to the lower power requirements of the connected components.

Figure 4:
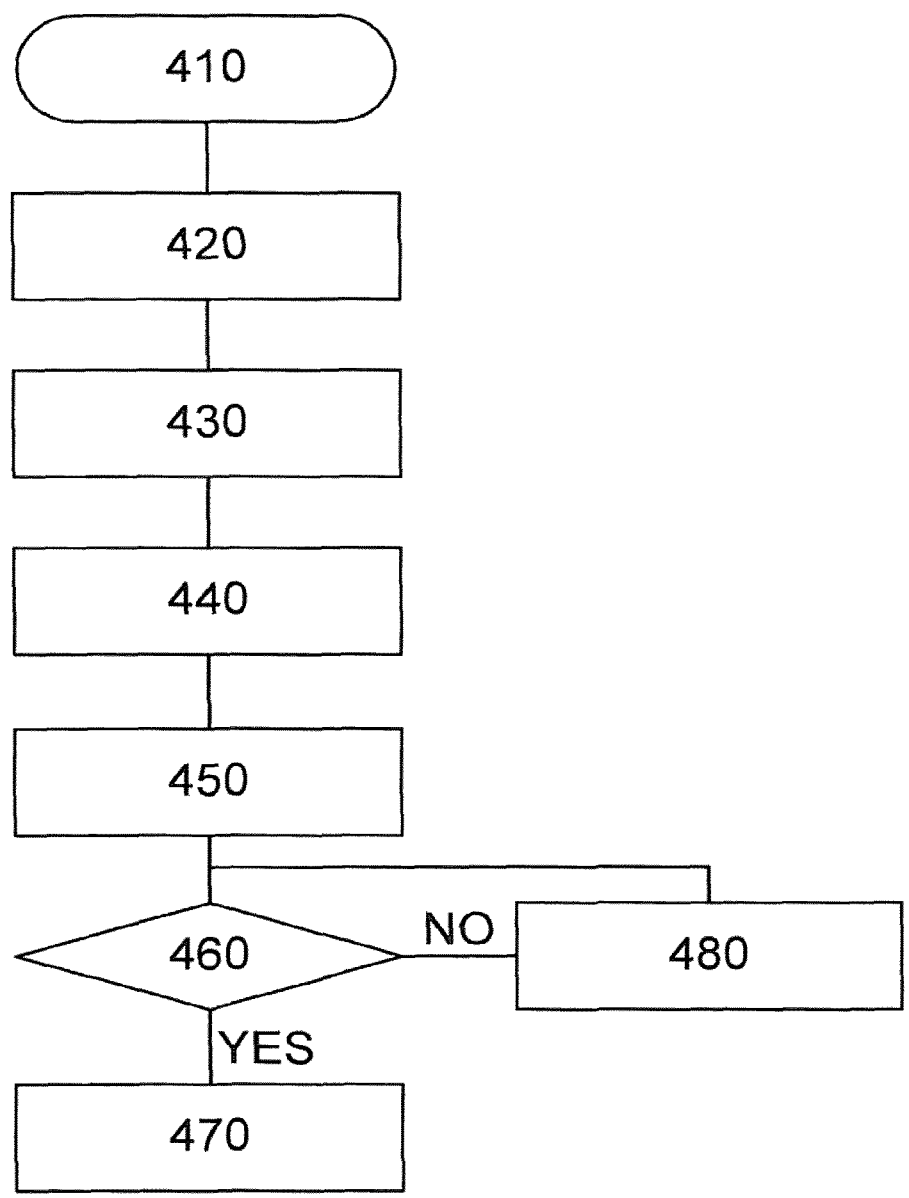
FIG. 4 is a flowchart of a powering down scheme for the device illustrated in FIG. 1 upon replacement of the end cap of the device in accordance with the second aspect of the present invention.

A typical use scenario is shown in FIG. 4. At step 410, the device 1 is operational, with the cap 12 removed from the device. As the cap 12 is off the device 1, the device 1 is on. The device may be in any number of operational modes—for example, injection mode, priming mode, cartridge exchange mode, dose history mode or the device may be idle on the main menu selection screen. Typically, the status of the device 1 is communicated to the user by the display 18.

At step 420, the cap 12 of the device 11 is placed onto the distal end 15 of the device, covering the needle mount 24 (and needle if present). When the cap 12 is properly secured, the magnet 102 aligns with the reed switch 100 (step 430) causing the switch 100 to open. After activation 430 of the switch 100, a signal is sent to the MPU 240 (step 440). The MPU 240 then queries the status of the device 10 by communicating with the first and second electrical circuits 200, 220 (step 450). Unless the first and/or second electrical circuits indicate that a critical operation is underway (decision point 460), the MPU terminates all other device operations and shuts down the device by actuating the electrical switching circuit 250, either directly or via the second electrical circuit, cutting power between the battery 205 and the first electrical circuit 200 (step 470).

If, at decision point 460, the device 1 indicates that it is active, for example the device is currently dosing, changing a cartridge or performing an activity that is critical to device operation, the device 1 is allowed to continue with the activity. Once the critical activity has completed, the device can shut down as indicated above. Alternatively, the user can be asked via the display 18 whether shutdown should proceed. In other words, the MPU 240 (and/or the second electrical circuit 220) holds the connection between the battery 205 and the first electrical circuit 200 until the critical device operation is complete. Once critical operations have completed, the MPU terminates all other device operations and shuts down the device by actuating the electrical switching circuit 250, either directly or via the second electrical circuit, cutting power between the battery 205 and the first electrical circuit 200 (step 470).

By preventing automatic shutdown of the device upon actuation of the cap switch 230, allowance can be made for unintentional or accidental actuation of the cap switch 230. In the example of the reed switch, high stray magnetic fields may inadvertently trigger the cap switch 230. Although such events may be rare, it is an important safety aspect that the device is able to recognise and prevent immediate shutdown such that the user is able to determine the state of the device prior to shutdown and at next use.

When the cap 12 is in place on the device, and the first electrical circuit 200 has been powered down, the electrical connection between the second electrical circuit 220 and the battery 205 is maintained. This allows the maintenance of the system clock 225 and allows the second electrical circuit 220 to monitor and recognise removal of the cap 12 (activation of the cap switch 230), without needing to power the larger first electrical circuit which has a higher power consumption requirement.

In alternative embodiments of the invention the second electrical circuit 220 is omitted. In such embodiments the cap switch 230 can be connected directly to the first electrical circuit 200, or it may act as a electrical switching circuit, such that upon actuation of the cap switch, the first electrical circuit is immediately disconnected from the battery 205.

The invention claimed is:

1. A hand-held medicament delivery device comprising:
    a housing containing a contactless switch, a first electrical circuit, and a battery;
    a medicament delivery mechanism; and
    a protective cap releasably securable to the housing, wherein the protective cap comprises a magnetic switch actuator configured to activate the contactless switch in response to the magnetic switch actuator being in proximity to the contactless switch, and wherein the contactless switch is operable between an on state in which the first electrical circuit is connected to the battery and an off state in which the first electrical circuit is disconnected from the battery.

2. The device of claim 1, wherein the contactless switch is a reed switch.

3. The device of claim 1, wherein the first electrical circuit comprises a display.

4. The device of claim 3, wherein the first electrical circuit further comprises a dose button configured to cause the medicament delivery mechanism to deliver a medicament dose.

5. The device of claim 3, wherein the first electrical circuit further comprises a motor of the medicament delivery mechanism.

6. The device of claim 3, wherein the first electrical circuit further comprises an illumination source configured to illuminate one or more user buttons.

7. The device of claim 1, further comprising:
one or more first components configured to receive power from the battery via the first electrical circuit;
a second electrical circuit coupled to the battery; and
one or more second components configured to receive power from the battery via the second electrical circuit.

8. The device of claim 7, wherein the one or more first components receive power from the battery when the contactless switch is in the on state, the one or more first components do not receive power from the battery when the contactless switch is in the off state, and the one or more second components receive power from the battery when the contactless switch is in the on state and the off state.

9. The device of claim 8, wherein the one or more second components operate using relatively less power than the one or more first components.

10. The device of claim 7, further comprising:
a switching circuit coupling the first electrical circuit to the battery,
wherein the second electrical circuit is coupled to the contactless switch and the switching circuit, and
wherein the switching circuit is configured to (i) disconnect the first electrical circuit from the battery responsive to the second electrical circuit indicating that the switch actuator is in proximity to the contactless switch and (ii) connect the first electrical circuit to the battery responsive to the second electrical circuit indicating that the switch actuator is not in proximity to the contactless switch.

11. The device of claim 7, further comprising a microprocessor coupled to the first electrical circuit and the second electrical circuit, wherein the microprocessor is configured to communicate with the first electrical circuit and the second electrical circuit to determine whether a predetermined operation is being performed by the medicament delivery device and, responsive to the determination, control whether the first electrical circuit receives power from the battery.

12. A method of controlling power in a hand held medicament delivery device, the device including a cap releasably securable to a housing, the cap including a magnetic actuator and the housing including a contactless switch, the method comprising:
powering a first electrical circuit using a battery connected to the first electrical circuit while the cap is removed from the housing, wherein the first electrical circuit includes a display device;
securing the cap to the housing;
responsive to securing the cap to the housing, the magnetic actuator actuating the contactless switch; and
responsive to the magnetic actuator actuating the contactless switch, disconnecting the first electrical circuit from the battery.

13. The method of claim 12, further comprising:
after disconnecting the first electrical circuit from the battery, removing the cap from the housing;
responsive to removing the cap from the housing, detecting that the magnetic actuator is not actuating the contactless switch; and
responsive to detecting the magnetic actuator is not actuating the contactless switch, connecting the first electrical circuit to the battery.

14. The method of claim 12, further comprising:
responsive to actuating the contactless switch, signaling to a microprocessor that the cap is secured to the housing; and
responsive to signaling that the cap is secured to the housing, the microprocessor determining whether the device is performing a predetermined operation,
wherein disconnecting the first electrical circuit from the battery is further responsive to
the microprocessor determining that the device is not performing the predetermined operation.

15. The method of claim 14, further comprising, responsive to the microprocessor determining that the device is performing the predetermined operation, prompting the user via the display device to provide an input indicating whether to disconnect the first electrical circuit from the battery.

16. The method of claim 14, further comprising, responsive to the microprocessor determining that the device is performing the predetermined operation, the microprocessor waiting until the predetermined operation is completed before causing the disconnection of the first electrical circuit from the battery.

17. The method of claim 14, wherein the predetermined operation comprises a dosing operation.

18. The method of claim 14, wherein the predetermined operation comprises changing a cartridge of the medicament delivery device.

19. The method of claim 14, wherein the predetermined operation comprises writing data to a memory of the medicament delivery device.

20. The method of claim 12, further comprising, while disconnecting the first electrical circuit from the battery, maintaining power to a second electrical circuit.

* * * * *